United States Patent [19]

Rogozinski

[11] Patent Number: 5,264,218
[45] Date of Patent: Nov. 23, 1993

[54] MODIFIABLE, SEMI-PERMEABLE, WOUND DRESSING

[75] Inventor: Wallace J. Rogozinski, Azusa, Calif.

[73] Assignee: C. R. Bard, Inc., Murray Hill, N.J.

[21] Appl. No.: 692,539

[22] Filed: Apr. 29, 1991

Related U.S. Application Data

[63] Continuation-in-part of Ser. No. 426,164, Oct. 25, 1989, abandoned.

[51] Int. Cl.⁵ ............................ A61F 13/00; A61L 15/00
[52] U.S. Cl. ................................. 424/445; 424/443; 424/78.02; 602/41; 602/42; 602/52; 428/41; 428/42; 428/43
[58] Field of Search .................. 424/445, 443, 448; 128/156; 428/41, 42, 43; 602/42, 41, 52

[56] References Cited

U.S. PATENT DOCUMENTS

| | | | |
|---|---|---|---|
| Re. 33,353 | 9/1990 | Heinecke | 428/41 |
| 4,561,435 | 12/1985 | McKnight et al. | 128/156 |
| 4,649,909 | 3/1987 | Thompson | 128/156 |
| 4,959,251 | 9/1990 | Owens et al. | 428/41 |

Primary Examiner—Thurman K. Page
Assistant Examiner—James M. Spear
Attorney, Agent, or Firm—G. Donald Weber, Jr.

[57] ABSTRACT

A dressing for wounds or dermal ulcers. The dressing includes a semi-permeable, transparent polyurethane film and a plurality of concentric polyethylene foam rings or disks. Application of foam rings to a semi-permeable thin film permits modification of the moisture/vapor transmission characteristic of the wound dressing which can be adjusted to suit the wound environment.

17 Claims, 1 Drawing Sheet

MODIFIABLE, SEMI-PERMEABLE, WOUND DRESSING

This is a continuation-in-part of application Ser. No. 07/426,164, filed Oct. 25, 1989, now abandoned.

BACKGROUND

1. Field of the Invention

This invention is directed to a wound dressing, in general, and to a wound dressing which permits the moisture and vapor transmission characteristics thereof to be coherently varied or adjusted, in particular.

2. Prior Art

Historically, wounds of both an acute and chronic nature have been treated with the traditional gauze and adhesive bandage coverings. However, in recent years, researchers have established that, in many respects, the traditional gauze and adhesive bandage coverings, as well as similar wound coverings, actually inhibit or even defeat the normal wound healing process by:

(1) Absorbing a significant amount of vital tissue fluid thereby dessicating tissue of the wound bed and, consequently, initiating dry tissue necrosis;

(2) Establishing a high rate of tissue fluid evaporation with the result that the dry gauze dressing abuts against and adheres to newly forming tissue which can induce secondary trauma upon removal of the dressing;

(3) Providing a portal of entry for infection causing micro-organisms into the wound; and/or (4) Enhancing the necrotizing effects of antiseptic irrigants by concentrating the active antimicrobial agent in the wound bed as a consequence of rapid evaporation of tissue fluid.

More recently, a transparent polyurethane, semi-permeable, wound covering has been developed. This type of covering has significantly eliminated many of the shortcomings of gauze bandages. For example, (1) A moist environment is created and maintained within the wound bed which has proven to be essential to wound healing;

(2) The polyurethane dressings are occlusive and, thus, help protect against secondary infection by preventing entry of micro-organisms to the wound site.

(3) The inherent moisture/vapor transmission properties of the film permit moderate amounts of wound exudate and tissue fluid to pass through the film;

(4) The frequency of dressing changes is dramatically reduced; and (5) A clinician can visually monitor the wound site through the transparent film.

Although transparent film wound dressings represent a significant advance over previous treatment protocols and dressings, there are definite limitations of polyurethane film dressings. For example, most, if not all, manufacturers of semi-permeable, polyurethane wound dressings, use the same process. This process is to coat the surface of an extruded thin film of polyurethane with a medically approved adhesive; apply a release liner; cut the film into various sizes; package and sterilize. Unfortunately, however, the application of an adhesive to the entire surface of the film dressing greatly reduces the ability thereof to transport moisture, gas and/or vapor by as much as 50% of the capability of the uncoated polyurethane film.

The adhesive coated film also presents end user handling and application difficulties that have yet to be resolved. For example, when removed from the release liner, the fully adhesive coated film becomes very flimsy and difficult for the user to manipulate, even when using two hands. If, by chance, two adhesive coated surfaces of the film (or portions thereof) make intimate contact, separation thereof becomes virtually impossible, thus, necessitating that the film be discarded.

Moreover, dressings using fully coated films are inadequate for moderate to heavily exudating wounds. In view of the significantly reduced moisture/vapor permeability of the adhesive coated films, moderate to heavily exudating wounds quickly overwhelm the ability of the film to transport moisture and vapor at a rate which curtails or eliminates exudate pooling.

Typically, when the volume of exudate is clearly visible through the dressing, the probability then of the exudate fluid passing by and through the adhesive seal of the film dressing which is in contact with the intact skin around the wound margin is extremely high. Once the seal of the adhesive is breached, the dressing is no longer of any value.

SUMMARY OF THE INSTANT INVENTION

This invention utilizes the full moisture vapor transmission potential of uncoated polyurethane film. A polyethylene foam ring is mounted to an uncoated polyurethane film. A disk is also supplied which is formed of a layer of polyethylene foam arranged in a plurality of concentric rings or annuli. When a portion of the disk is detached and applied over the film, the moisture vapor transmission characteristic of the dressing is modified by occlusion.

DESCRIPTION OF THE PREFERRED EMBODIMENT

Figure 1:
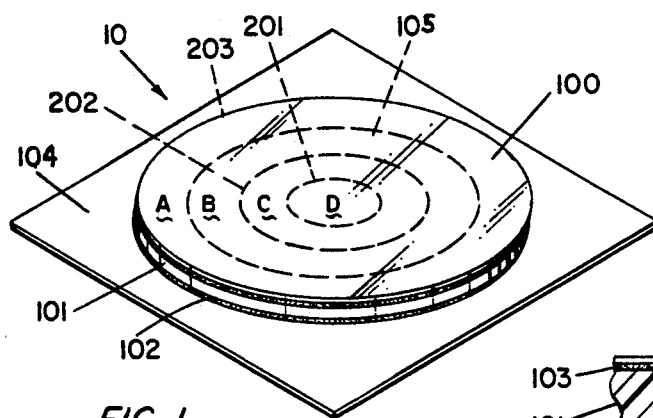
FIG. 1 is an isometric view of one embodiment of the wound dressing of the instant invention.

Concurrent reference is now made to FIGS. 1 through 5 wherein common components bear common reference numerals.

Referring now to FIG. 1, there is shown an isometric view of dressing 10 fabricated in accordance with the instant invention. The dressing 10, as shown in its assembled form prior to actual usage, includes a lower release liner 104 which is easily handled by the consumer. A layer 101 of polyethylene foam (or similar lightweight material) is adhered to the liner 104 by an adhesive layer 102. In the preferred embodiment, the layer of foam is formed in the shape of a disk cut into a plurality of concentric rings A, B, C and D by concentric cuts 201, 202, and 203 (shown dashed). A layer of release liner 105 overlies all but the outermost rings (in this case, ring A). A film 100 of polyurethane (or similar semi-permeable material) is adhered to the outermost ring of the foam 101 by an adhesive layer 103. The film 100 is characterized by a relatively high moisture vapor transmission rate.

The dressing 10 is used by removing the lower release liner 105 as well as the inner concentric rings B, C and D. The outer ring A is mounted on the patient, over the wound, and adhered thereto by the adhesive layer 102. The polyurethane film 100 (to the extent the undersurface thereof is exposed after removal of the inner concentric rings) overlies the wound and is spaced therefrom by the foam disk 101.

Figure 2:
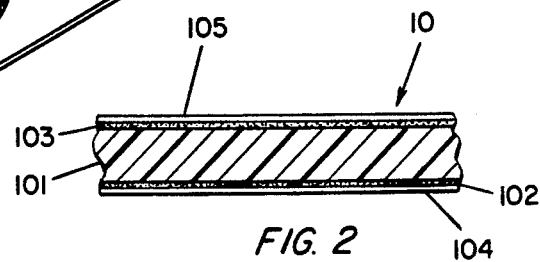
FIG. 2 is a cross-sectional view of an intermediate assembly developed in the production of the dressing shown in FIG. 1.

Referring now to FIG. 2, there is shown a representative cross-sectional view of an intermediate composite developed while fabricating the dressing 10 of the instant invention (sometimes referred to as a VARI-MOIST TM or a HI-MOIST TM dressing). As shown, a support layer 101 formed of polyethylene foam is provided. Typically, the foam layer 101 is about 0.625" thick. However, the layer 101 can have a suitable thickness, typically, in the range of about 0.03" to about 1.0". These thicknesses are deemed typical but not limitative.

Also, as shown in FIG. 2, the polyethylene foam layer 101 (which can take the form of an extruded polyethylene foam sheet) is coated on both major surfaces. The coatings 102 and 103 are medically approved adhesives such as Avery 1-780 acrylic. These adhesive layers are applied in any suitable manner such as via rollers or the like. The layers are quite thin and conformable. Also, the adhesive coatings adhere to the foam layer 101.

A release liner 104 is applied over the lower adhesive coating 102. A release liner 105 is applied over the upper adhesive coating 103. The release liners are, typically, thin layers of glazed paper, plastic or the like and are conventional in the art. The release liners 104 and 105 are selected to be readily "peelable" from the adhesive layers 102 and 103, respectively. That is, the liners are removable and do not remove the adhesive coating from the foam layer 101. Preferably, the release liners should be of a relatively inert material which will not contaminate the adhesive coatings or any other portion of the dressing 10. All of these layers are assembled in a suitable fashion using conventional equipment and the time/temperature profiles for the assembly process are known in the art. Typically, the layers are assembled in the arrangement shown in FIG. 1 but in the form of continuous strips.

Figure 3:
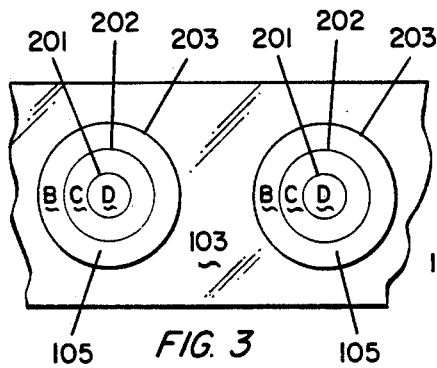
FIG. 3 is a top plan view of the laminar assembly shown in FIG. 1 after a first cutting operation.

After the layers are assembled as shown in FIG. 2, a cutting die (not shown), typically of circular configuration, is utilized to cut the laminar assembly as shown in FIG. 3. In particular, the cutting die includes one or more concentric blades, typically of extremely sharp, surgical steel, or the like. The cutting die (not shown) is selected to cut through the layers of the laminar assembly shown in FIG. 2 to (but not through) bottom release liner 104. Thus, a plurality of concentric rings B, C, and D or annuli of the laminar assembly are produced as shown in FIG. 3. The numbers and diameters of the concentric rings of the laminar assembly are defined by the cuts 201, 202, 203 and so forth made by the cutting die.

Figure 4:
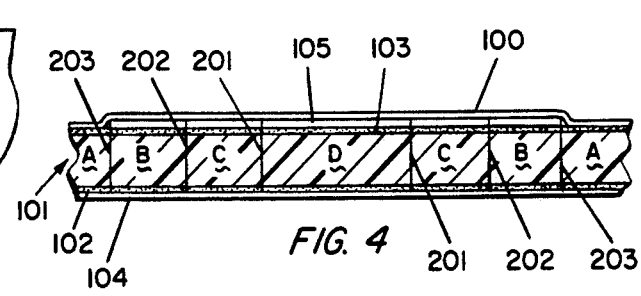
FIG. 4 is a cross-sectional view of another intermediate assembly developed in the production of the dressing shown in FIG. 1.

As shown in FIG. 4, the cuts 201, 202, 203 and so forth do not pass through lower release liner 104. Thus, liner 104 serves as an overall support for all of the concentric rings produced in the composite, laminar structure by the cutting die.

Once the die cut is completed, a portion of the upper release liner 105 is remove. In particular, the portion of the liner 105 which is outside of the outer cut (in this embodiment, cut 203) is removed thereby exposing the adhesive coating 103 as shown in FIG. 3.

As shown in FIG. 4, a polyurethane film 100 is applied over the entire upper surface of the composite structure. In this case, the film 100 is applied to the adhesive surface 103 and over the remaining concentric rings of liner 105. Typically, the film 100 is produced with a thickness of about 0.5 mil. The expected useful range of film thickness is from about 0.5 mil to about 3.0 mil. These thicknesses are deemed typical but not limitative. The film 100 bonds to only the exposed surface of adhesive coating 103, i.e. where the portion of liner 105 outside of cut 203 has been removed.

Figure 5:
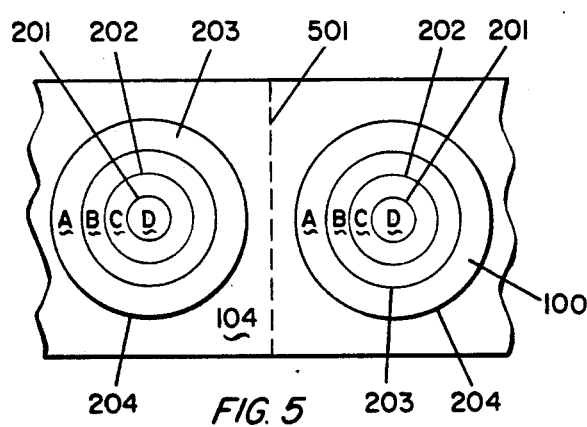
FIG. 5 is a top plan view of the dressing shown in FIG. 2 with an outermost cutting accomplished.

The laminar assembly, including film 100, is then passed through a second cutting and stamping procedure, for example. In this step, another cutting die (not shown) is used to produce an outer circular cut 204 in the dressing, as shown in FIG. 5. Again, the cut 204 passes through all of the layers, including film 100, but does not pass through the lower liner 104. The film 100 and excess foam 101 (as well as any other layers except the lower release liner 104) external to the outer cut 204 is then trimmed away by a stamping die (not shown). This operation produces a plurality of concentric rings mounted on a lower liner and surmounted by a polyurethane film. Another cutting die or any other suitable processing equipment (not shown) can be used to cut through the liner 105 on the cut line 501 (shown dashed) to produce a rectilinear shaped lower-release liner 104 wherein the four corners of the bottom release liner 104 are exposed. This arrangement permits the liner 104 to be grasped by the user in order to separate the foam ring/film laminate dressing 10 from the liner 104 (see FIG. 5) for use.

Figure 6:
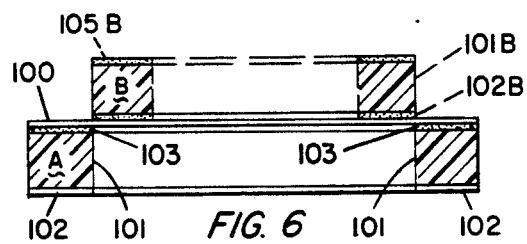
FIG. 6 is a cross-sectional view of the dressing shown in FIG. 2 with a portion thereof removed and ready for application to a wound.
Figure 7:
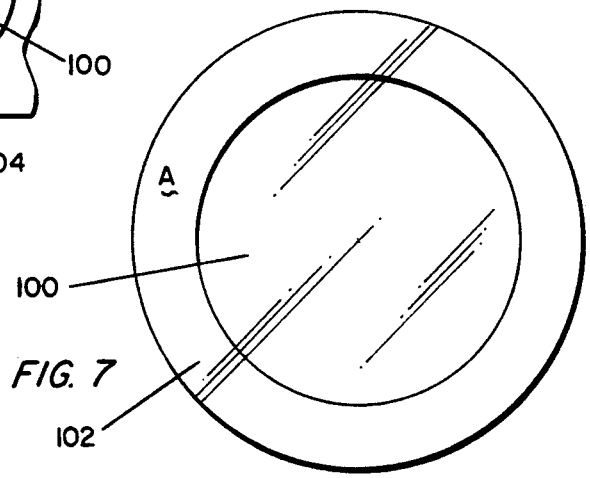
FIG. 7 is a bottom plan view of the dressing ready for application to a wound.

As shown in FIGS. 6 and 7, the dressing 10 is ready for application. That is, the lower liner 104 has been removed, along with the interior concentric rings B, C and D. The lower adhesive layer 102 of concentric ring A is now exposed as a result of the removal of the lower release liner 104 (See FIG. 6). The inner surface of the center portion of the polyurethane film 100 is uncoated inasmuch as it has previously been disposed over the liner 102. (The outer surface was not coated at any time.) However, the outer edge of film 100 is adhered to the upper surface of the outermost ring A of foam 101 as shown in FIG. 4.

The foam/film dressing 10 is then placed over an open wound or ulcer with adhesive 102 adhering to the skin of the patient. With the dressing in place, the film 100 portion of the dressing 10 is unimpeded by any adhesive coating and can function at the maximum moisture/vapor transport rate to suitably control moderate to heavily exudating wounds without the typical exudate pooling and overflow problems frequently experienced with the dressings known in the art which utilize coated films.

However, wounds and ulcers (dermal) are very often quite individual. Some long standing ulcers, for example, produce very little exudate fluid and appear to be dry. It would be inappropriate to utilize a dressing 10 that exhibited a high vapor/moisture transmission rate with this kind of wound as further evaporation of tissue fluid might be detrimental to the patient's health.

The dressing 10 of this invention permits the selective modification of the moisture/vapor transport of the film 100 by selectively limiting the surface area of the uncoated polyurethane film 100 in dressing 10 which is utilized. For example, if a wound or dermal ulcer is assessed as exudating, i.e. producing mild to moderate exudate fluid, it is treated with this invention as follows:

1. The outermost ring A of the film/foam ring (between cuts 203 and 204) is grasped and removed from the release liner 104 backing.

2. The dressing 10 (comprising ring A and film 100) is placed over the wound and the edges of the foam ring A with the adhesive layer 102 are gently pressed onto the skin surrounding the wound margin.

3. At this point the wound is evaluated and one or more of the inner rings B,C and D is removed from the release liner 104 and placed over the film portion 100 of the dressing 10 which is in place over the wound.

Thus, if a wound is producing exudate, only the basic dressing 10 (i.e. ring A and film 100) is used. If the wound is assessed to be dry to moist, the above outlined procedure is followed except, that foam rings B and C are placed over film 100. These rings are removed from the release liner 104 placed on the outer surface of film 100. In FIG. 6, ring B (shown dashed) is shown in place atop film 100 as an example. The inner rings carry the adhesive coating 102 and adhere to the film 100. Also, the inner rings carry the liner 105 which, together with the foam ring, impedes the moisture/vapor transmission of the film 100.

By using more and more concentric foam rings and thereby progressively reducing the available surface of film 100 which can transport moisture/vapor, the evaporation rate of the tissue fluid of the wound can be controlled to insure an optimum wound environment. The advantage of the Vari-Moist TM wound care system is that it can treat a broad range of wound types. Additionally, the handling problems associated with fully coated films are eliminated with Vari-Moist TM or HI-MOIST TM.

Thus, there is shown and described a modifiable, semi-permeable wound dressing. Clearly, the preferred embodiments have been described. While this description is directed to a particular embodiment, it is understood that those skilled in the art may conceive modifications and/or variations to the specific embodiments shown and described herein. However, any such modifications or variations which fall within the purview of this description are intended to be included therein as well. It is understood that the description herein is intended to be illustrative only and is not intended to be limitative. Rather, the scope of the invention described herein is limited only by the claims appended hereto.

I claim:

1. A medical dressing comprising,
an annular support means formed of a lightweight polymeric material of thickness about 0.03 to 1", and;
a continuous film of polymeric semi-permeable material of thickness about 0.0005 to 0.003" permitting moisture vapor transmission therethrough joined to said upper surface of said annular support means and spanning said central opening, said film and said annular support means defining a central void area within said annular support means; and
an adhesive means on the lower surface of said annular support means for selectively adhering said annular support means to a skin surface surrounding a wound so that said central void area is disposed between the wound and said film which is thereby spaced away from the skin surface.

2. The dressing recited in claim 1 wherein, said annular support means is formed of polyethylene.

3. The dressing recited in claim 1 wherein, said film is formed of polyurethane.

4. The dressing recited in claim 1 wherein, said film is joined to the upper surface of said annular support means by an adhesive material.

5. The dressing recited in claim 1 including
at least one circular element of said lightweight material having a diameter which is smaller than said annular support means,
said circular element mounted on a surface of said film opposite said annular support means and opposite said central void area.

6. A modifiable medical dressing formed by the process steps of:
placing an upper and lower layer of adhesive on respective upper and lower surfaces of a thin layer of polymeric foam material of thickness about 0.03 to 1";
placing an upper and a lower release liner on the respective upper and lower layers of adhesive;
making a plurality of concentric cuts through the upper release liner, both through the adhesive layers and said layer of foam material, but not through said lower release liner;
removing a portion of the upper release liner which is external to the outermost of said concentric cuts;
covering with a thin polymeric semi-permeable film of thickness about 0.0005 to 0.003" the remaining upper release liner and the adhesive layer exposed by the removal of the portion of the upper release liner; and
making an additional cut which is concentric to the prior cuts, external thereto, and through the film and each of the other layers except the lower release liner.

7. A medical dressing comprising,
a layer of polymeric foam material of thickness about 0.03 to 1" having a plurality of concentric cuts therethrough to form a plurality of concentric rings of foam material including an outer concentric ring;
a first release liner releasably adhered to a first surface of all of said concentric rings;
a second release liner releasably adhered to a second surface of all but outer concentric ring; and
a polymeric semi-permeable film of thickness about 0.0005 to 0.003" adhered to the second surface of said said outer concentric ring and covering the second release liner.

8. The dressing recited in claim 6, formed by the additional step of trimming away foam material and film external to said additional cut.

9. The dressing recited in claim 8, formed by the additional steps of separating said lower release liner from said lower surface and removing the concentrically cut foam material not adhered to said film to define a central void area in said foam material.

10. A medical dressing comprising,
a support layer of lightweight polymeric material of thickness about 0.0005 to 0.003" having at least one continuous internal cut therethrough so as to produce an outer member and an inner member;

a thin, continuous layer of polymeric permeable material of thickness about 0.0005 to 0.003" which exhibits a moisture vapor transmission rate therethrough, adhered by a first surface to the upper surface of at least said outer member of said support layer; and an adhesive layer on the lower surface of said support layer whereby the lower surface of said outer member of said support layer can be adhered to a skin surface and said inner member of said support layer can be separated from said outer member and selectively adhered to a surface of said thin layer opposite said first surface and juxtaposed over a space originally occupied by said inner member thereby to occlude at least a portion of said thin layer and control the moisture vapor transmission therethrough.

11. The dressing recited in claim 10 additionally including, a release liner selectively adhered to the lower surface of said support layer by said adhesive layer.

12. The dressing recited in claim 10 wherein, said support layer has a plurality of continuous cuts therethrough so as to produce an outer member and a plurality of independent inner members, any of which may be adhered to the opposite surface of said thin layer.

13. The dressing recited in claim 12 wherein, said plurality of continuous cuts are arranged concentrically.

14. The dressing recited in claim 10 wherein, said support layer and said thin layer are non-absorbent.

15. The dressing recited in claim 7 wherein, said film exhibits a high moisture vapor transmission rate.

16. The dressing recited in claim 3 wherein, said film exhibits a high moisture vapor transmission rate.

17. The dressing recited in claim 9, formed by the additional step of adhering at least a portion of removed foam material to a surface of said film opposite said exposed adhesive layer and opposite said central void area.

* * * * *